US009442125B2

(12) United States Patent
Pouteau et al.

(10) Patent No.: US 9,442,125 B2
(45) Date of Patent: Sep. 13, 2016

(54) METHOD AND A DEVICE FOR CHARACTERIZING THE COAGULATION OR SEDIMENTATION DYNAMICS OF A FLUID SUCH AS BLOOD OR BLOOD PLASMA

(71) Applicant: COMMISSARIAT A L'ENERGIE ATOMIQUE ET AUX ENERGIES ALTERNATIVES, Paris (FR)

(72) Inventors: Patrick Pouteau, Meylan (FR); Magalie Faivre, Grenoble (FR); Philippe Peltie, Saint Paul de Varces (FR); Anne Planat-Chretien, St Egreve (FR)

(73) Assignee: Commissariat a L'Energie et aux Energies Alternatives, Paris (FR)

( * ) Notice: Subject to any disclaimer, the term of this patent is extended or adjusted under 35 U.S.C. 154(b) by 0 days.

(21) Appl. No.: 14/925,495

(22) Filed: Oct. 28, 2015

(65) Prior Publication Data
US 2016/0047828 A1 Feb. 18, 2016

Related U.S. Application Data

(62) Division of application No. 12/469,200, filed on May 20, 2009.

(51) Int. Cl.
| | |
|---|---|
| G01N 33/86 | (2006.01) |
| G01N 33/50 | (2006.01) |
| G01N 21/49 | (2006.01) |
| G01N 21/47 | (2006.01) |
| G01N 33/49 | (2006.01) |
| G01N 21/75 | (2006.01) |
| G06T 7/00 | (2006.01) |

(52) U.S. Cl.
CPC ............. *G01N 33/86* (2013.01); *G01N 21/49* (2013.01); *G01N 21/75* (2013.01); *G01N 33/4905* (2013.01); *G06T 7/0016* (2013.01); *G01N 2201/06113* (2013.01); *G01N 2201/12* (2013.01); *G06T 2207/10016* (2013.01); *G06T 2207/30004* (2013.01); *G06T 2207/30024* (2013.01)

(58) Field of Classification Search
CPC ...... G01N 33/68; G01N 33/50; G01N 33/48; G01N 33/00; G01N 21/49; G01N 21/25; G01N 21/17; G01N 21/00
USPC .......................................................... 436/69
See application file for complete search history.

(56) References Cited

U.S. PATENT DOCUMENTS

| | | | |
|---|---|---|---|
| 3,635,678 A | 1/1972 | Seitz et al. | |
| 4,252,536 A | 2/1981 | Kishimoto et al. | |
| 4,756,884 A | 7/1988 | Hillman et al. | |
| 5,408,326 A | 4/1995 | Wang | |
| 6,352,630 B1 | 3/2002 | Frenkel et al. | |
| 6,801,311 B1 | 10/2004 | Fuhr et al. | |
| 7,737,088 B1 * | 6/2010 | Stahler ................. | B01J 19/0046 435/6.19 |

OTHER PUBLICATIONS

Piederriere Y. et al, Speckle and Polarization for Biomedical Applications, Proc. of SPIE, vol. 6341, Sep. 2006, pp. 634006.1-634106.5.*
Search Report for European Application No. EP 10 29 0082 dated Jul. 22, 2010.
Office Action for European Application No. 10 290 082.6 dated Jun. 1, 2011.
Preliminary Search Report for France Appl. No. FR 0901435 completed Oct. 27, 2009.
Office Action for U.S. Appl. No. 12/469,200 dated Nov. 2, 2011.
Office Action for U.S. Appl. No. 12/469,200 dated May 16, 2012.
Office Action for U.S. Appl. No. 12/469,200 dated May 6, 2014.
Office Action for U.S. Appl. No. 12/469,200 dated Septemer 19, 2014.
Office Action for U.S. Appl. No. 12/469,200 dated Mar. 10, 2015.
Office Action for U.S. Appl. No. 12/469,200 dated Jul. 9, 2015.
Chicea, D., *Results of Sediment Motion Visualization by a Modified LASCA Technique*, Proc. of SPIE vol. 6785 (2007), 7 pages.
Kalchenko, V. et al., *In Vivo Dynamic Light Scattering Imaging of Blood Coagulation*, Journal of Biomedical Optics, vol. 12, No. 5, Sep./Oct. 2007, pp. 952002-1-052002-4.
Nadkarni, S. K. et al., *Characterization of Atherosclerotic Plaques by Laser Speckle Imaging*, Circulation, Aug. 9, 2005, pp. 885-892.
Piederriere, Y. et al., *Evaluation of Bood Plasma Coagulation Dynamics by Speckle Analysis*, Journal of Biomedical Optics, vol. 9, No. 2, Mar./Apr. 2004, pp. 408-412.
Piederriere, Y.,: *Etude du Speckle de Milieux Diffusants Liquides. Application a la Determination de Parametres Biophysiques*, L'Universite de Bretange Occidentale, U.F.R. Sciences et Techniques de Brest, Brest, (Dec. 15, 2003), XP002591394, 164 pages.
Rajan, V. et al., *Speckle Size and Decorrelation Time; Space-Time Correlation Analysis of Coherent Light Dynamically Scattered From Turbid Media*, Optics Communications 281 (2008) 1755-1760.
Office Action for U.S. Appl. No. 14/469,200 dated Mar. 18, 2016.
Piederriere, "*Study of the Speckle of Liquid Scattering Media. Application for the determination of biophysical parameters.*", Dec. 15, 2003.

* cited by examiner

*Primary Examiner* — Christine T Mui
(74) *Attorney, Agent, or Firm* — Alston & Bird LLP

(57) ABSTRACT

A method of characterizing the coagulation or sedimentation dynamics of a fluid such as whole blood, a blood fraction, or blood plasma, the method including: illuminating a sample of the fluid with a beam of coherent light; acquiring a time series of images of a speckle pattern generated by interaction between the sample and the spatially coherent light beam; and processing the time series of images; wherein the processing step includes calculating a function representative of the variation in the speckle pattern between two or more images of the series. The invention also provides a device for implementing such a method.

16 Claims, 6 Drawing Sheets

METHOD AND A DEVICE FOR CHARACTERIZING THE COAGULATION OR SEDIMENTATION DYNAMICS OF A FLUID SUCH AS BLOOD OR BLOOD PLASMA

CROSS REFERENCE TO RELATED APPLICATION

This application is a divisional of U.S. application Ser. No. 12/469,200 filed May 20, 2009, which claims priority from French Application No. 09 01435, filed Mar. 26, 2009, which is hereby incorporated herein in its entirety by reference.

FIELD OF THE INVENTION

The invention relates to a method of characterizing the coagulation or sedimentation dynamics of a fluid such as whole blood, a blood fraction, or blood plasma, and also to a device for implementing such a method.

BACKGROUND OF THE INVENTION

Measuring the coagulation time of blood is of great medical interest. Coagulation disorders can lead to severe physiological disturbances such as abundant bleeding during surgery or wounds that bleed excessively (coagulation time too long), or such as thromboses or embolisms (coagulation time too short). Very many diseases, pathologies, medical treatments, or therapy follow-ups require such coagulation time to be checked on a more or less regular basis. Frequently this involves blood being taken from a vein, which requires intervention by a specialist. The sample taken is then analyzed in a specialized laboratory, where various different tests can be performed for measuring coagulation time, depending on the pathology or the treatment of the patient under analysis. Mention can be made in particular of the following: Quick's prothrombin time (PT or QT); activated cephalin time (ACT); and kaolin cephalin time (TCK). Frequently, it is not directly the absolute values of these coagulation times that are of interest for clinicians, but rather their ratios relative to reference times for the same test, performed on a reference sample made up from a pool (or mixture) of fifty or more samples from patients deemed to be normal. In addition, the measured coagulation time depends on the physical method used for characterizing the coagulation phenomenon, on the way in which the sample is mixed with the coagulation factor under study (mixing time), and on the reagent used for triggering the reaction. It is therefore common practice to apply a correction in order to obtain a result that is independent of these factors. By way of example, mention can be made of the international normalized ratio (INR) that is calculated on the basis of the prothrombin time divided by the reference time and raised to the power ISI (international sensitivity index) as given by the manufacturer of the batch of reagents used for implementing the tests.

Conventionally, measuring blood coagulation time involves the following steps.

In a first step, the blood is taken from the patient in a tube that contains a suitable anticoagulant giving a reasonable amount of time for transport between the place where the sample is taken and the place where it is analyzed (a minimum of several minutes) without the sample coagulating.

Thereafter, the plasma is extracted from the blood sample by centrifuging and is mixed in the appropriate proportions with various reagents needed for inhibiting the anticoagulant that was used when taking the sample (e.g. calcium ions), and with the reagents needed for triggering coagulation (e.g. thromboplastin), depending on the factor under study.

Finally, coagulation time proper is measured with the help of various kinds of equipment.

Document U.S. Pat. No. 4,252,536 describes an optical device and method for measuring coagulation time. That device and method are based on variation in the intensity of a detected optical signal as a result of a modification in diffusion through a plasma sample during the formation of a coagulated blood clot.

Document U.S. Pat. No. 3,635,678 describes another method in common use, consisting in introducing a magnetic bead into the plasma sample, and putting the bead into oscillatory motion with the help of an external magnet or electromagnet. The movement of the bead is observed optically. The measured time at the end of which the bead freezes in the plasma, being held stationary by the clot that is forming, corresponds to the coagulation time.

Those methods are not suitable for use with whole blood, since it is too opaque.

Document U.S. Pat. No. 6,352,630 describes an electrochemical method of measuring coagulation time. Implementing that method requires a consumable comprising electrodes that come into contact with the biological sample, equipment that serves to relay the electrical contacts on the consumable, and the addition to said sample of electrochemical agents enabling measurement to be performed.

The article by Yann Piederriére et al. entitled "Evaluation of blood plasma coagulation dynamics by speckle analysis" describes two methods of studying the dynamics of blood coagulation by analyzing laser speckle.

Those methods are based on the observation that the particles (platelets, proteins) in suspension in the plasma diffract and diffuse light; if the plasma sample is illuminated by a laser beam that is spatially and temporally coherent, a speckle pattern appears. Because of the brownian movement of the particles, the pattern varies over time so long as the plasma remains liquid, and then freezes once the clot has formed.

In the first method described in the above article, the light intensity corresponding to one point of the speckle pattern is registered as a function of time. That method is quite difficult to implement: the transparency of the plasma decreases during the coagulation process; it is therefore necessary to increase the illumination light intensity over time, or to illuminate the sample rather strongly throughout the duration of acquisition, at the risk of saturating the detector. Furthermore, since the light intensity at only one point is taken into consideration, the optical signal is weak, thereby implying an unsatisfactory signal-to-noise ratio, unless the illumination light intensity used is relatively high.

The second method described in that article involves acquiring a time series of images of the speckle pattern, and in determining the contrast in each image. Before the clot forms, the brownian movement of the particles in suspension "scrambles" the image, thereby reducing their contrast. Contrast increases when the speckle pattern freezes as a result of the plasma coagulating. As admitted by the authors, that method does not enable coagulation time to be determined accurately.

All of the above-described methods make use of plasma, and cannot operate with whole blood. They therefore require a prior step of fractioning the blood, and that can be performed only in a specialized laboratory.

SUMMARY OF THE INVENTION

The invention seeks to overcome at least some of the drawbacks of the prior art. In particular, the device and the method of the invention enable coagulation dynamics to be studied both of whole blood and of plasma. In addition, they are simple and inexpensive to implement, at the site of treatment, and they provide results that are accurate.

Furthermore, the invention also makes it possible to study the dynamics of blood sedimentation, and that also is of medical interest.

In one aspect, the invention provides a method of characterizing the coagulation or sedimentation dynamics of a fluid such as whole blood, a blood fraction, or blood plasma, the method comprising:
  illuminating a sample of said fluid with a beam of coherent light. The term "coherent" light, is used here and throughout the present application, to designate light that is spatially and temporally coherent, such as that produced by a laser light source;
  acquiring a time series of images of a speckle pattern generated by interaction between said sample and said spatially coherent light beam; and
  processing said time series of images;
  wherein said processing step includes calculating a function representative of the variation in said speckle pattern between two or more images of the series.

The method of the invention differs from that known from the above-mentioned article by Yann Piederriére et al. essentially by the image processing it implements. In the prior art method, each speckle image is considered independently of the others, and is processed in such a manner as to provide an overall numerical value (contrast) that is indicative of the fluidity of the sample; the variation in those numerical values over time provides the required information about coagulation dynamics. In contrast, in the invention, two successive images acquired at different instants are analyzed together, pixel by pixel; it is only after this combined analysis that an "overall" numerical value is calculated that is indicative of the change in the speckle pattern between two image acquisition instants.

Testing performed by the inventors shows that the data processing method implemented by the invention provides results that are much more accurate than in the prior art. In addition, unlike the prior art, the invention is also suitable for studying the coagulation of whole blood, and not only of plasma (even though the reasons for this are not well understood).

In various implementations of the invention:
  Said processing step may also include determining a coagulation or sedimentation time from said function representative of the variation of said speckle pattern between two or more images of the series.
  Said processing step may include calculating a correlation function between successive image pairs.
  Said processing step may include identifying a point of inflection in said correlation function.

The method may also include determining the time variation in the optical transmission of said sample, and using said variation to discriminate between coagulation dynamics and sedimentation dynamics. Advantageously, the time variation in the optical transmission of said sample may be determined from said time series of images, e.g. by analyzing the sum of the intensities of the pixels in a zone of the image.

Said images may be acquired at a rate greater than or equal to 0.5 hertz (Hz).

Advantageously, the sample may be constituted by whole blood mixed with reagents, the optical path length of said spatially coherent light beam through said sample lying in the range 20 micrometers ($\mu m$) to 1000 $\mu m$, preferably in the range 30 $\mu m$ to 300 $\mu m$. When plasma is used instead of whole blood, this length may be significantly longer, since plasma contains a smaller density of light-diffusing particles. Thus, the use of whole blood for determining coagulation time presents two advantages: firstly it makes the prior centrifuging step superfluous; and secondly it enables the device for characterizing coagulation to be miniaturized.

In another aspect, the invention also provides a device for implementing a method as described above for characterizing the coagulation or sedimentation dynamics of a fluid, the device comprising:
  a microfluidic device having a fluid flow passage suitable for receiving a sample of said fluid and enabling it to be illuminated;
  lighting means for illuminating said sample by a spatially coherent light beam;
  an image sensor for acquiring a time series of images of an optical speckle pattern generated by interaction between said sample and said coherent light beam; and
  processor means for processing said time series of images;
  wherein said processor means are adapted to calculate a function representative of the variation of said speckle pattern between two or more images of the series.

In various embodiments of the invention:
  Said image sensor may be offset relative to the direct path of said spatially coherent light beam so as to avoid being dazzled.
  Said image sensor may be lens-free.
  Said lighting means and said image sensor may be arranged on two opposite sides of the fluid flow passage, which passage is transparent, thereby causing said images to be acquired by transmission. Under such circumstances, said fluid flow passage may be of thickness lying in the range 20 $\mu m$ to 1000 $\mu m$, preferably in the range 30 $\mu m$ to 300 $\mu m$.
  Alternatively, said lighting means and said image sensor may be arranged on the same side of the fluid flow passage, a reflecting element being provided on the opposite side therefrom, whereby said images are acquired by reflection. Under such circumstances, said fluid flow passage may have thickness lying in the range 25 $\mu m$ to 500 $\mu m$, and preferably in the range 50 $\mu m$ to 150 $\mu m$.

BRIEF DESCRIPTION OF THE DRAWINGS

Other characteristics, details, and advantages of the invention appear on reading the following description made with reference to the accompanying drawings given by way of example, and in which.

MORE DETAILED DESCRIPTION

As is well known in optics, a diffusing article or a rough surface that is subjected to laser radiation (or more generally to radiation that is spatially and temporally coherent) forms a granular image because of the diffraction effects generated by the roughness or the diffusion centers, and because of interference between individual diffraction patterns. This granular effect is known as "speckle".

Figure 1:
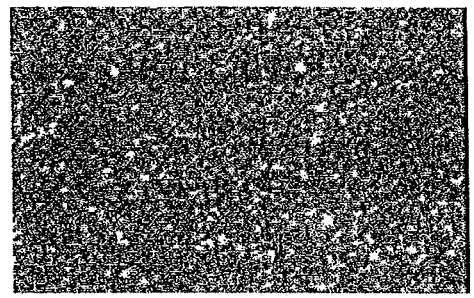
FIG. 1 is an image showing the speckle of a sample of whole blood.

FIG. 1 shows the image of speckle from a sample of whole blood, in which the cells (white and red corpuscles) and the other particles in suspension in the plasma (platelets, large proteins) act as centers of light diffusion.

The particles in suspension in a blood sample are animated with unceasing movement; the speckle image therefore varies over time until it freezes once the blood has coagulated completely and formed a solid clot. It is this effect that enables coagulation time to be measured in accordance with the invention.

As shown in FIGS. 2A to 3B, a device for implementing the method of the invention comprises a microfluidic chamber CMF, that is at least partially transparent, a lighting source using light that is spatially and temporally coherent, such as a semiconductor laser or a helium-neon laser L, and a camera C. Reference M designates a mirror used for directing the laser beam towards the fluidic chamber.

In the exemplary embodiment of the invention, the microfluidic chamber used comprises two glass slides spaced apart by spacers and held 160 μm apart. It is initially placed on the measurement bench.

A quantity of 10 microliters (μL) of whole blood is added to 20 μL of Neoplastine (registered trademark), a mixture of thromboplastin and of calcium chloride, as manufactured by Stago Diagnostics.

Figure 2A:
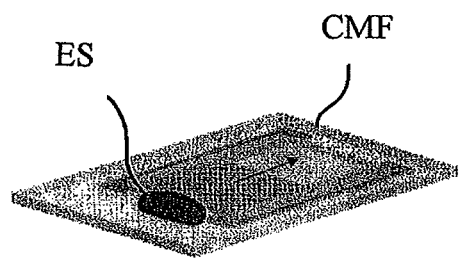
FIGS. 2A and 2B show a microfluidic chamber used as a sample carrier.
Figure 2B:
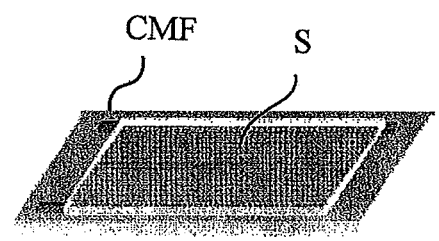

The solution is homogenized by being successively sucked into and expelled from a micropipette, and 20 μL of the mixture are deposited at the inlet of the microfluidic chamber, which then becomes filled merely by migration under capillarity as shown in FIGS. 2A and 2B, where the reference ES indicates the sample constituted by the blood and the reagents.

Measurement is triggered when the reagents are put into presence. There is therefore a delay, typically of the order of ten to a few tens of seconds, between the beginning of the measurement and the time when it is actually possible to view images that correspond to the chamber being full, and subsequently to coagulation. The initial measurement instant is taken as being the moment of mixing.

The dimensions of the microfluidic device CMF and the volume of blood and of reagents specified above are merely indications, and are not in any way limitations on the invention. More generally, with whole blood, the microfluidic passage defined by the chamber CMF may be of thickness lying in the range a few tens of micrometers to about 1 millimeter (mm). If the thickness is too small, then there are not enough particles on the path of the light beam, and the contrast in the speckle image is not sufficient; if the thickness is too great, then light absorption by the blood will give an image that is too dark to be usable.

Figure 3A:
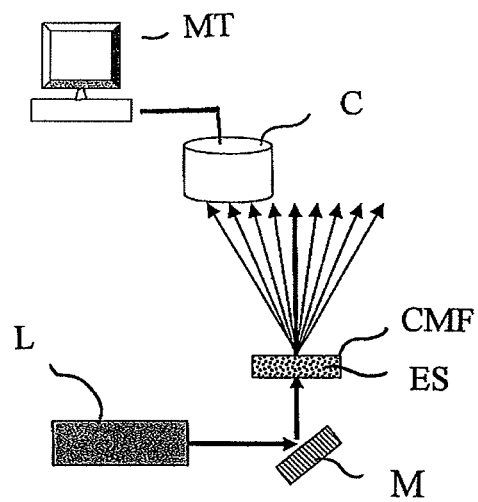
FIGS. 3A and 3B are diagrams corresponding to two embodiments of a device of the invention.

FIG. 3A is a diagram showing a first implementation of the invention in which the microfluidic chamber CMF is entirely transparent, e.g. being constituted by two glass slides, and measurement is performed by transmission. For this purpose, the illuminating light beam of coherent light is incident on the chamber CMF via a first side thereof, and the camera C is arranged on the opposite side. It should be observed that the camera C is offset relative to the path of the light beam in the absence of any diffusion and/or diffraction, in order to avoid dazzling the camera.

As mentioned above, the light source L may typically a helium-neon laser or a semiconductor laser. The wavelength of the radiation is advantageously about 650 nanometers (nm) to 690 nm, so as to enable good penetration into blood. Lighting power lying in the range 100 microwatts (μW) to a few milliwatts (mW), or a few tens of milliwatts, can suffice.

The thickness of the microfluidic chamber CMF may generally lie in the range 20 μm to 1000 μm, and preferably in the range 30 μm to 300 μm.

The area of the incident light beam at the microfluidic chamber preferably lies in the range about 10 square micrometers ($\mu m^2$) to a few square millimeters ($mm^2$), with the dimensions of the microfluidic chamber being adjusted accordingly.

The camera C is essentially constituted by an image sensor of the type having a charge-coupled device (CCD) matrix or having an image sensor made of CMOS (complementary metal oxide on silicon) technology, located at a distance of a few centimeters or a few tens of centimeters from the microfluidic chamber (such a propagation distance is needed to enable a speckle image to form), without using a focusing system. Sampling may be modest: a sensor having 30 pixels☐30 pixels has been used with results that are satisfactory. Specifically, the camera may be of the "webcam" type with its lens removed, or it may be the optical system of a laser computer mouse.

The rate at which images are acquired does not need to be particularly high: a rate of 0.5 Hz has been found to be satisfactory for studying the dynamics of blood coagulation. Too high a rate is of no use: the time interval between two successive images must be not less than the characteristic time of variation in the speckle image.

The acquisition time for each image may advantageously be 50 milliseconds (ms), or even less if the light intensity is sufficient. Too long an acquisition time leads to a decrease in speckle contrast, since the movement of the particles in suspension can then be sufficiently fast to make the image fuzzy.

Figure 3B:
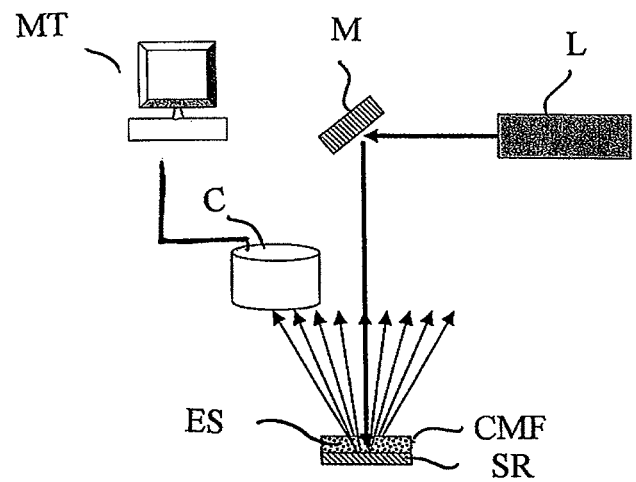

FIG. 3B is a diagram of a second implementation of the invention in which the microfluidic chamber CMF is constituted by a top slide that is transparent and a substrate SR that is reflective, e.g. a substrate made of silicon. Under such circumstances, the laser beam passes through the transparent slide and the sample, and is then reflected in part on the substrate SR, passing back through the sample, and the signal is subsequently detected by the camera C placed on the same side of the sample as the laser L. This configuration can be advantageous, for example if the sample needs to be stirred or heated by means of a module located beneath the microfluidic chamber. It may also make it possible to incorporate a device of the invention in a microfluidic chip made of silicon, plastics material, and glass. Such a microfluidic chip may have feed means, a zone for mixing with reagents, whether in liquid or dry form, and previously placed in the microfluidic chamber, a zone enabling the mixture to be homogenized, by optionally-external disturbances (acoustic stirrer), and followed by an analysis zone. The reagents used may be dry, e.g. freeze-dried. The analysis zone may also be placed in the zone where mixing is performed with dry reagents. The feed means may be constituted directly by a sample-taking needle, with blood being sucked in either by capillarity, or by suction. Heater means and temperature control means may be applied in contact with or in the vicinity of the microfluidic chamber.

In this second implementation of the invention, the thickness of the microfluidic passage may be half that of the first implementation so as to obtain the same optical path length through the sample.

Whatever the implementation used, the images acquired by the camera C are digitized and transferred to data processor means MT in real or deferred time, which data processor means may typically be a laptop or office computer provided with suitable software, or a component of the digital signal processor (DSP) type suitable for processing images directly, it also being possible for the processor means to be incorporated directly in the image-taking silicon chip.

As mentioned above, the essential image processing step of the invention is represented by calculating a function that is representative of the variation in said speckle pattern between two or more images acquired at different instants.

Several functions of this type may be envisaged.

A first possibility consists in calculating, pixel by pixel, the difference in intensity between two successive images, and in summing the absolute values of these differences between two images in order to obtain a value for the variation between two successive images:

$$f_1 = \sum_{i=1}^{N} |x_i - y_i|$$

where:
N is the total number of pixels;
$x_i$ (with i=1 to N) are the intensity values for the pixels of one image; and
$y_i$ are the intensity values for the pixels of the image preceding or succeeding $\underline{x}$.

A second possibility consists in calculating the correlation factor $\underline{r}$ between two successive images so as to obtain a value for the variation between the two images:

$$f_2 = r = \frac{\sum_{i=1}^{N} \sqrt{(x_i - \bar{x})^2} \times \sqrt{(y_i - \bar{y})^2}}{\sqrt{\sum_{i=1}^{N}(x_i - \bar{x})^2} \times \sqrt{\sum_{i=1}^{N}(y_i - \bar{y})^2}}$$

where:
N is the total number of pixels;
$x_i$ (with i=1 to N) are the intensity values of the pixels of an image;
$\bar{x}$ is the mean intensity value for image $\underline{x}$, i.e.:

$$\bar{x} = \frac{1}{N}\sum_{i=1}^{N} x_i$$

$y_i$ are the intensity values of the pixels of the image preceding or succeeding $\underline{x}$; and
$\bar{y}$ is the mean intensity value for image $\underline{y}$, i.e.:

$$\bar{y} = \frac{1}{N}\sum_{i=1}^{N} y_i$$

Figure 4A:
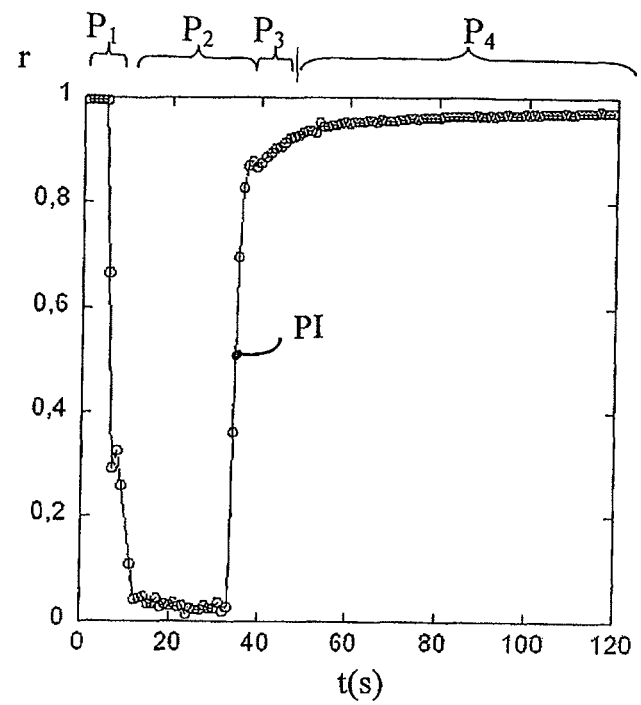
FIGS. 4A and 4B are graphs showing respectively a correlation curve obtained by a method of the invention operating on whole blood, and its derivative.

FIG. 4A is a graph plotting a curve representing the value of the correlation coefficient $\underline{r}$ as a function of time $\underline{t}$ (in seconds), obtained under the above-described experimental conditions. The acquisition rate was 1 Hz and the acquisition time 50 ms.

Four stages can be seen in the curve.

Initially (stage $P_1$) the microfluidic chamber CMF is empty. There is no speckle variation and the correlation factor $\underline{r}$ is close to 1 (it would be exactly 1 if there were no noise, neither in the electronics nor in the optics).

Thereafter, the blood is introduced in the microfluidic chamber and the correlation coefficient drops suddenly.

During the second stage $P_2$, preceding coagulation proper, the correlation coefficient remains very low. Between one image and the following image, the speckle pattern changes significantly because of the movements of the particles in suspension in the blood plasma. It is advantageous to recall that during this stage a cascade of reactions takes place in preparation for coagulation.

Coagulation proper, i.e. when the blood cells slow down or cease moving, occurs during a third stage $P_3$ during which the correlation factor increases quickly. When the coagulation factor used is thromboplastin, this is known as the prothrombin time.

The coagulation time TC is defined, in conventional manner, as the instant at which the curve r(t) presents a point of inflection PI (Quick's prothrombin time, marked TQ, corresponds to the coagulation time TC when the coagulating factor is thromboplastin). During the fourth and last stage $P_4$, the correlation coefficient $\underline{r}$ hardly changes, indicating that a clot has formed, thereby freezing the particles in suspension and consequently freezing the speckle pattern. The still-remaining serum allows cells to move a little, which is why the correlation coefficient is not strictly equal to 1.

Figure 4B:
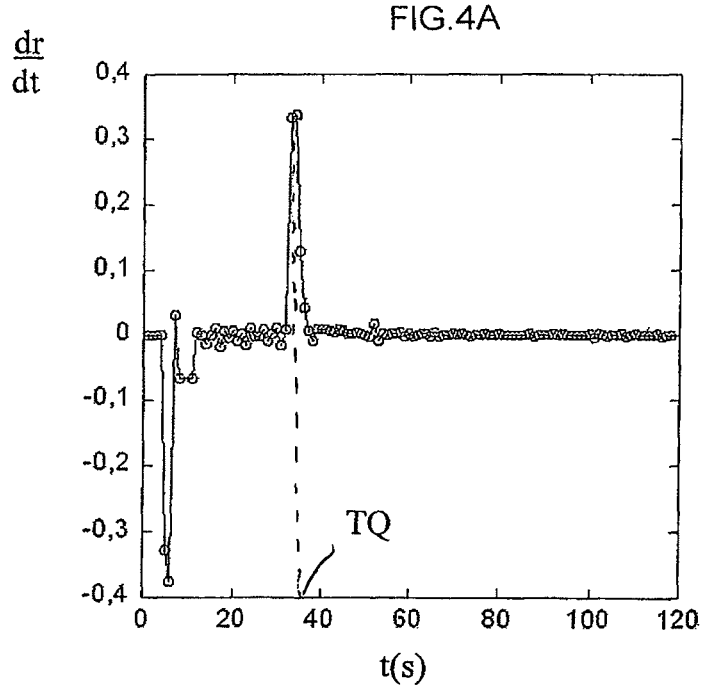

The point of inflection PI may be determined by identifying a local maximum in the time derivative of r(t), as shown in FIG. 4B.

The method of the invention has been repeated 20 times with blood from the same healthy donor, in order to test its repeatability. The mean measured coagulation time was 34 seconds (s) with a standard deviation of 1.5 s, corresponding to a coefficient of variation of 4.5%, which is very satisfactory given the fact that measurement triggering was performed manually.

The performance of the technique has been evaluated over a measurement range that is representative of real of variability amongst individuals, the individuals combining healthy donors and donors presenting pathologies. This evaluation was performed on the basis of 66 patients in the premises of Hospices Civils de Lyon (HCL). The measurement technique of the invention was compared with a conventional technique of measuring the optical transmission of the plasma, as is performed in that hospital analysis laboratory.

The following table summarizes the characteristics of the two techniques:

|  | Reference (HCL) | Invention |
| --- | --- | --- |
| Measurement system | MDA machine, from Trinity Biotech: optical transmittance measurement | Correlation of laser speckle images |
| Sample | 10 µL of plasma taken from a 5 mL tube of centrifuged citrate anticoagulated blood | 10 µL of citrate anticoagulated whole blood |
| Temperature | 37° C. | Ambient |
| Measurement replication | 1 | 3 |
| Time range | 10 s-60 s | 25 s-150 s |
| Duration of analysis | 20 min centrifuging + 20 min in machine = 40 min | 7 min |
| Coefficient of variation | <5% | <10% |

Figure 5A:
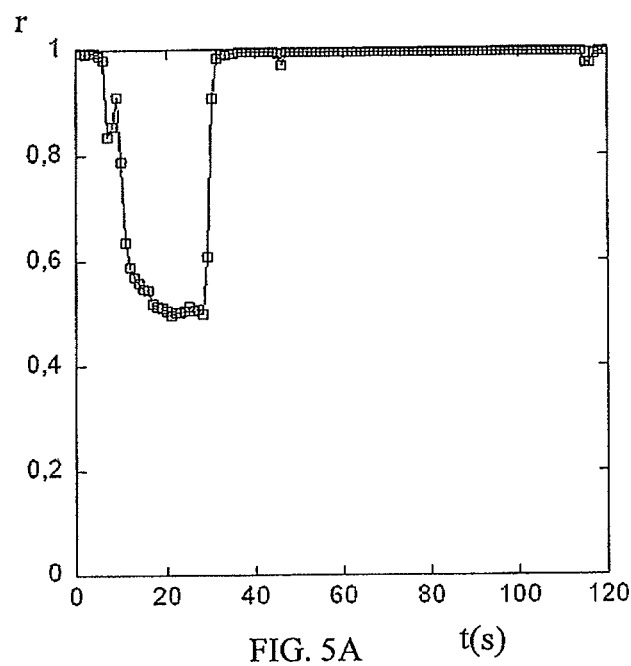
FIGS. 5A and 5B are graphs showing respectively a correlation curve obtained by a method of the invention and operating on plasma, and its derivative.
Figure 5B:
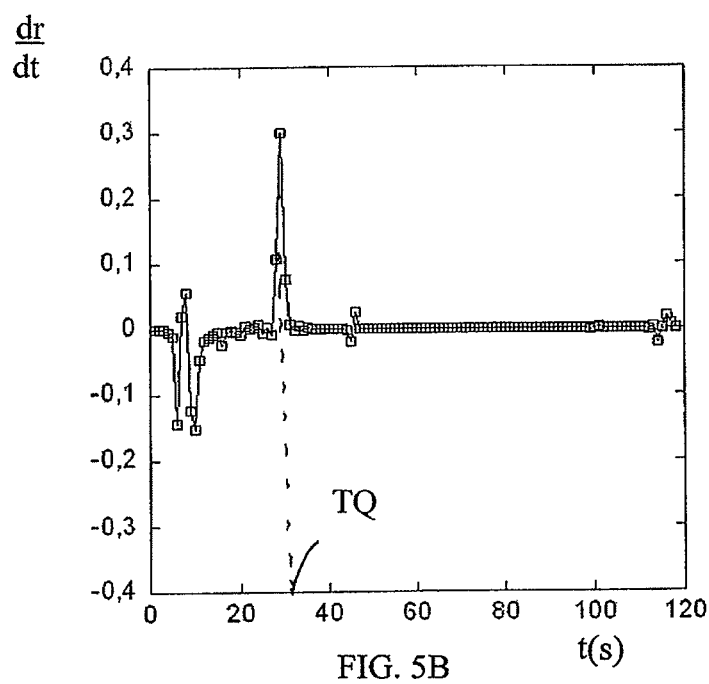

FIGS. 5A and 5B correspond to FIGS. 4A and 4B respectively, but relate to a measurement performed on blood plasma. The thickness of the fluid passage was 50 µm both times. It can be seen that the method of the invention gives results that are satisfactory even under such circumstances; nevertheless, the variation in the correlation coefficient is smaller because the density of diffusers is much smaller in plasma (where the diffusers are essentially platelets and proteins) than in whole blood (where the contribution from cells is dominant).

Figure 6A:
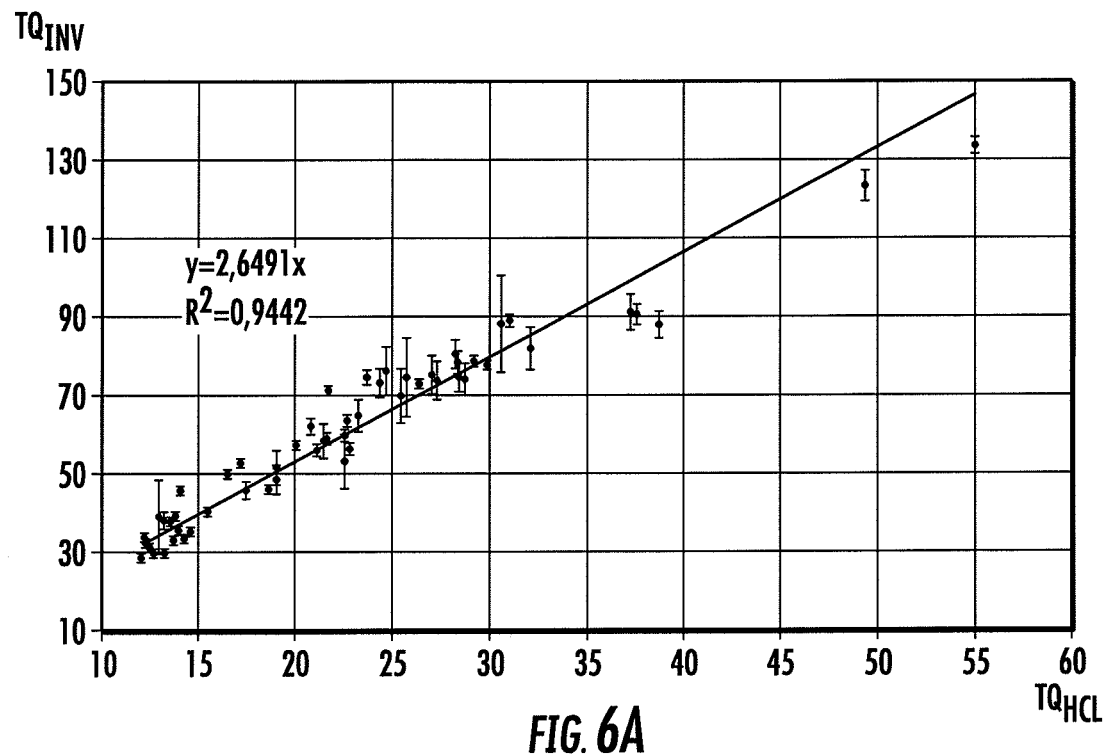
FIGS. 6A and 6B are graphs serving to compare the results obtained by applying the technique of the invention with results obtained by conventional methods of measuring prothrombin time (6A) and of measuring INR (6B)

FIG. 6A shows the correlation line for Quick's prothrombin time measured by the method of the invention, $TQ_{INV}$ and Quick's prothrombin time measured by the reference method $TQ_{HCL}$. It can be seen that even if the absolute time values do not coincide, they present a very good regression coefficient for the regression line (regression coefficient $R^2$ greater than 0.94). The correlation would be even better if no account were taken of two samples where $TQ_{HQL}>40$ s, which correspond to medical emergency situations in which use of the device and of the method of the invention is not intended.

As explained above, clinicians are not particularly interested in coagulation time as such, but above all in standardized parameters such as INR which is defined by the following formula:

$$INR = (TQ/TQ_R)^{ISI}$$

where:
TQ is the coagulation time (Quick's prothrombin time) of the sample under consideration;
$TQ_R$ is a reference time, corresponding to the prothrombin time of a reference sample; in the example considered here, $TQ_R=12$ s for the HCL method, and $TQ_R=34$ s for the method of the invention; and
ISI is a correction factor that depends on the reagents used for triggering coagulation; in the example considered here, ISI=1.3 for both methods.

Figure 6B:
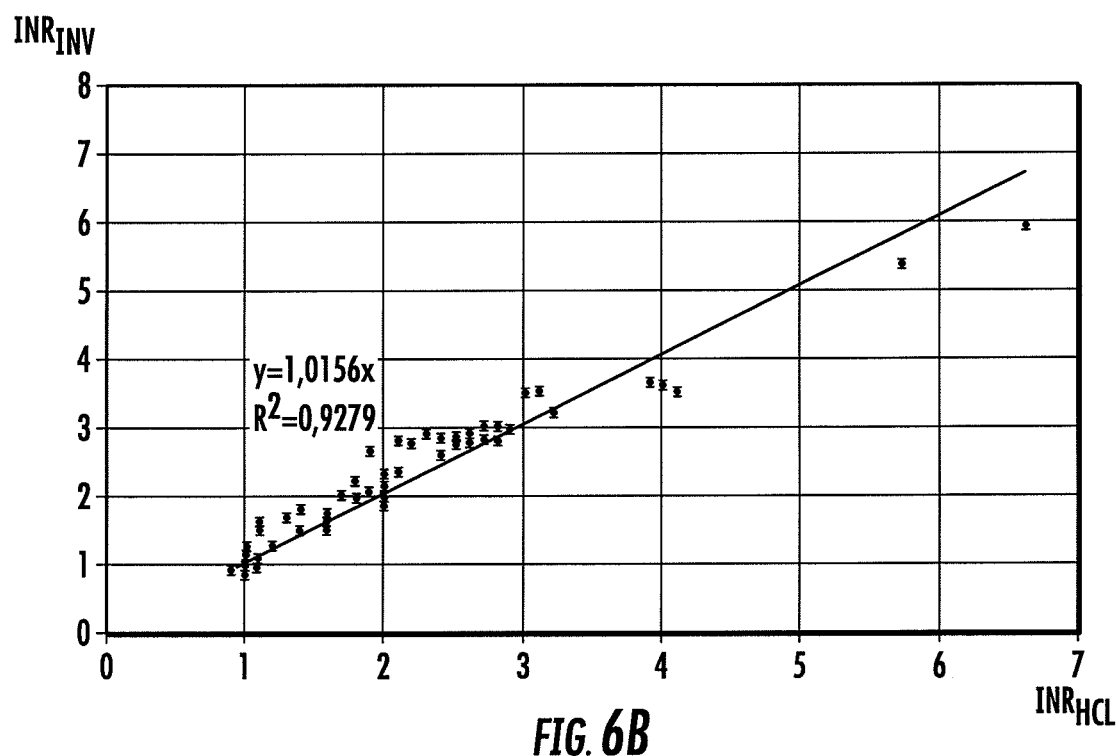

FIG. 6B plots the correlation line for INR as obtained with the reference method ($INR_{HCL}$, abscissa axis) and for the method of the invention ($INR_{INV}$, ordinate axis). It can be seen that the correlation is very good (regression coefficient=0.93) and the slope of the line is close to 1.

The method of the invention has been tested with samples of whole blood, which is advantageous for the reasons mentioned above. Nevertheless, there arises the problem of any potential influence of the hematocrit content of the samples on the measured correlation time.

Figure 7:
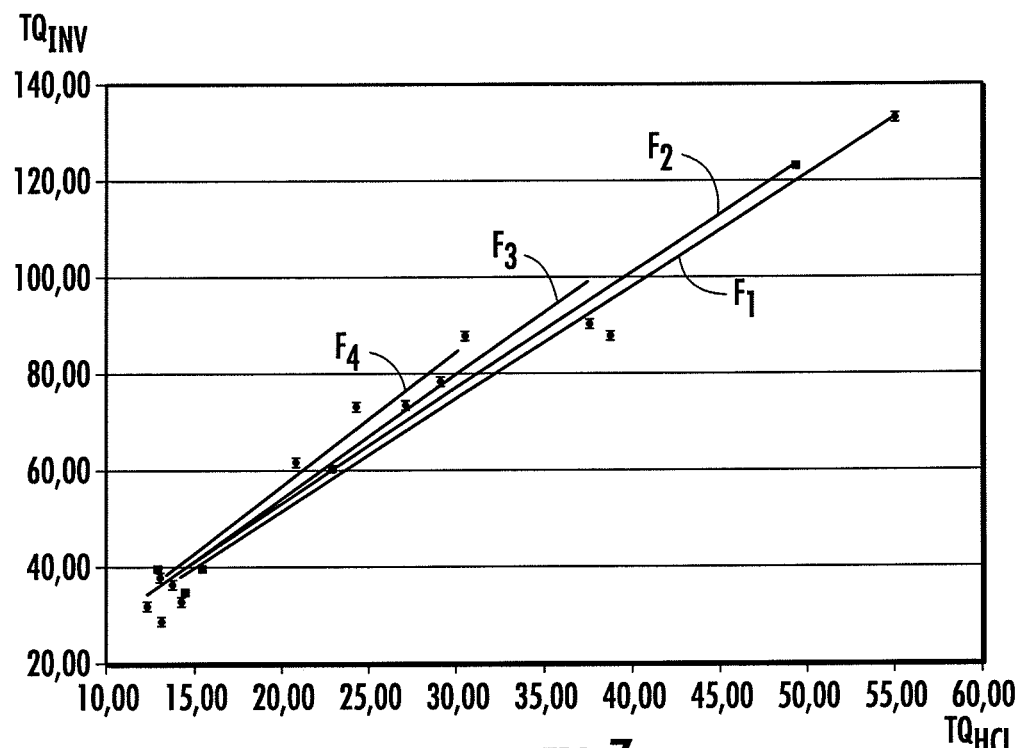
FIG. 7 is a graph showing the small influence of hematocrit on the results obtained when applying the technique of the invention.

To study this effect, the samples of whole blood were subdivided into four families as a function of their hematocrit contents:
F1: hematocrit less than 31%;
F2: hematocrit lying in the range 31% to 36%;
F3: hematocrit lying in the range 36% to 40%; and
F4: hematocrit greater than 40%;
and the corresponding correlation lines $TQ_{INV}/TQ_{HCL}$ are plotted in FIG. 7.

The slopes of the correlation lines for the various families are close together, with a maximum difference of about 10%, confirming that there is no significant influence from the hematocrit content on the measurement of coagulation time by the method of the invention.

Figure 8:
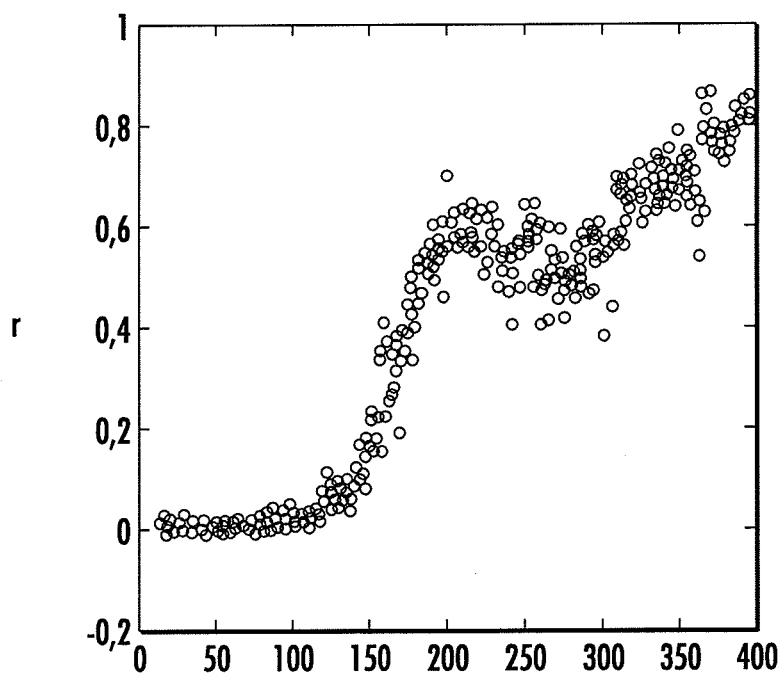
FIG. 8 is a graph showing the variation in the correlation obtained by a method implementing the invention on a sample of blood and caused by cell sedimentation.

In the absence of reagent for triggering the coagulation phenomenon, e.g. when measuring natural coagulation time, a phenomenon of sedimentation can occur involving blood cells settling under the effect of their own weight. This effect, like coagulation, also leads to an increase in the correlation coefficient between speckle pattern images, as shown in FIG. 8.

The speed of sedimentation is associated with a large number of parameters involving the blood under test, such as the number of red corpuscles, their volume, the contents of certain proteins, and the viscosity of the blood. This parameter is not directly specific of a disease, but it can help to direct diagnosis.

As explained above, blood coagulation is accompanied by a decrease in optical transmission through the sample, and thus to a decrease in the mean light intensity recorded by the camera. In contrast, sedimentation does not lead to any significant variation in the optical transmission through the sample. Measuring both the correlation coefficient and the mean light intensity thus enables these two phenomena to be distinguished.

Figure 9A:
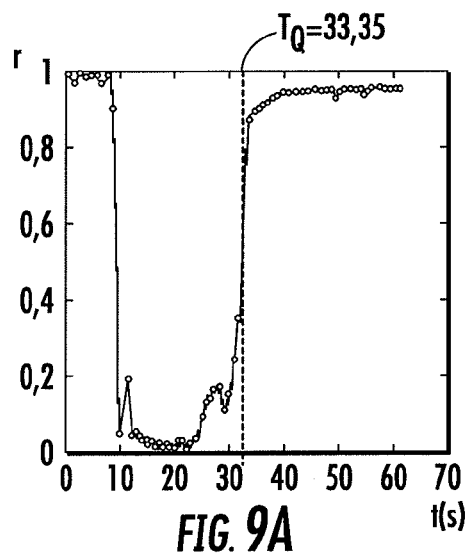
FIGS. 9A, 9B, 9C and 10A, 10B, 10C are graphs enabling the method of the invention to be compared with the method described by the above-mentioned article by Yann Piederriére et al.
Figure 9B:
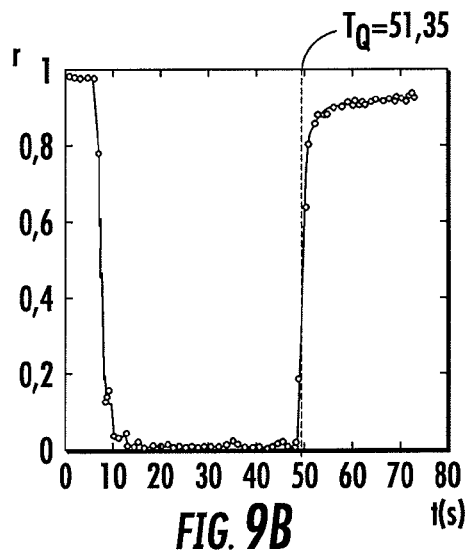
Figure 9C:
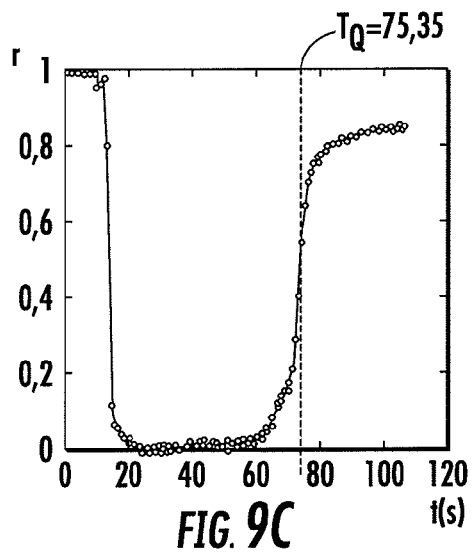

FIGS. 9A, 9B, and 9C show the variation over time of the correlation coefficient between speckle images, as measured in accordance with the invention, for three whole blood samples from three different patients. The measured coagulation times TQ were respectively 33.3 s, 51.3 s, and 75.3 s.

Figure 10A:
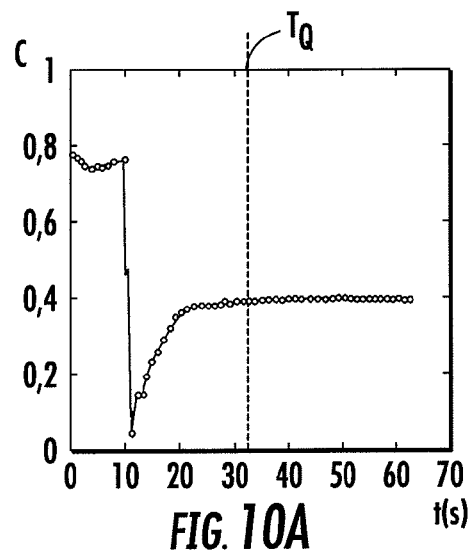
Figure 10B:
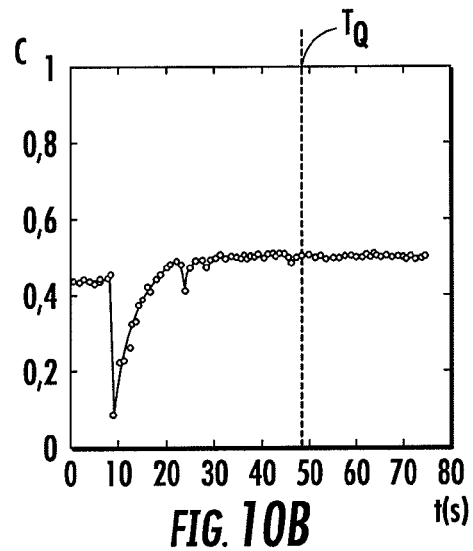
Figure 10C:
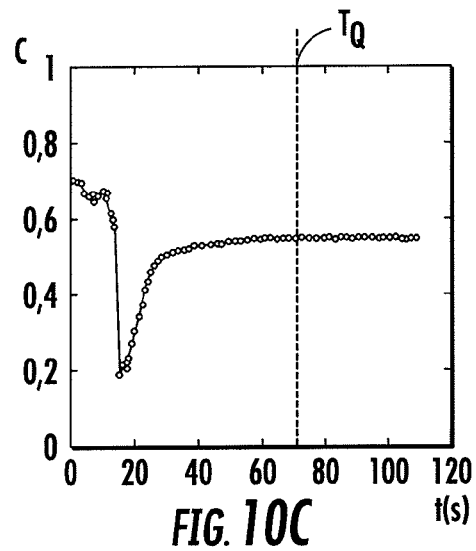

FIGS. 10A, 10B, and 10C show the variation in the contrast time C of the speckle images. Contrast is defined in the above-mentioned article by Y. Piederriére.

It can be seen that contrast C changes quickly over a much shorter time than TQ, and then presents a "tail" in which variation is very slow, thus preventing coagulation time from being determined accurately. Comparing these two sets of figures thus shows the advantage provided by the method of the invention.

In particular, while taking measurements that enable the natural coagulation time to be determined (time without a coagulation agent), it is possible to limit the effect of sedimentation by placing the microfluidic chamber on stirrer means, e.g. a plate that generates acoustic waves.

The invention is described above more particularly in its application for studying phenomena of coagulation and/or sedimentation in whole blood. Nevertheless, it can also be used for studying the dynamic behavior of coagulation, sedimentation, or drying in other fluids or suspensions.

What is claimed:

1. A method of characterizing the coagulation or sedimentation dynamics of a fluid such as whole blood, a blood fraction, or blood plasma, the method comprising:
introducing a sample into a device comprising:
a microfluidic device having a microfluidic chamber suitable for receiving a sample of said fluid and enabling it to be illuminated;
a lighting means positioned relative to the microfluidic device to illuminate said microfluidic chamber and said sample by a spatially coherent light beam;
a two-dimensional matrix image detector configured and arranged relative to the microfluidic device to acquire a time series of two-dimensional images of an optical speckle pattern generated by interaction between said sample and said spatially coherent light beam, wherein said two-dimensional images include pixels; and
a non-transient computer readable memory programmed with a computer software, the software configured, with a processor, to obtain a series of two-dimensional images from said two-dimensional matrix image detector, and calculate a function based on a difference between pixels or a correlation of two or more images of the series, and to characterize one or more of the coagulation or sedimentation of said fluid based on said function;
illuminating the sample of said fluid with a beam of coherent light;
acquiring a time series of two-dimensional images of a speckle pattern generated by interaction between said sample and said spatially coherent light beam, wherein said two-dimensional images include pixels; and
processing said time series of two-dimensional images;
wherein said processing step includes calculating a function, with the processor, based on a difference between pixels of two or more two-dimensional images of the series or on a correlation of two or more two-dimensional images of the series, and characterizing one or more of the coagulation or sedimentation of said fluid based on said function.

2. A method according to claim 1, wherein said processing step also includes determining a coagulation or sedimentation time from said function.

3. A method according to claim 1, wherein said processing step includes calculating a correlation function between successive image pairs.

4. A method according to claim 2, wherein said processing step includes calculating a correlation function between successive image pairs and identifying a point of inflection in said correlation function.

5. A method according to claim 1, also including determining the time variation in the optical transmission of said sample, and using said variation to discriminate between coagulation dynamics and sedimentation dynamics.

6. A method according to claim 5, wherein the time variation in the optical transmission of said sample is determined from said time series of two-dimensional images.

7. A method according to claim 1, wherein said two-dimensional images are acquired at a rate greater than or equal to 0.5 Hz.

8. A method according to claim 1, wherein the sample is constituted by whole blood mixed with reagents, the optical path length of said spatially coherent light beam through said sample lying in the range 20 µm to 1000 µm.

9. A method of characterizing the coagulation or sedimentation dynamics of a fluid, the method comprising:
illuminating the sample of said fluid with a beam of coherent light;
acquiring a time series of two-dimensional images of a speckle pattern generated by interaction between said sample and said spatially coherent light beam, wherein said two-dimensional images include pixels; and
processing said time series of two-dimensional images;
wherein said processing step includes calculating a function, with the processor, based on a difference between pixels of two or more two-dimensional images of the series or on a correlation of two or more two-dimensional images of the series, and characterizing one or more of the coagulation or sedimentation of said fluid based on said function.

10. The method according to claim 9, wherein said processing step also includes determining a coagulation or sedimentation time from said function.

11. The method according to claim 9, wherein said processing step includes calculating a correlation function between successive image pairs.

12. The method according to claim 9, wherein said processing step includes calculating a correlation function between successive image pairs and identifying a point of inflection in said correlation function.

13. The method according to claim 9, also including determining the time variation in the optical transmission of said sample, and using said variation to discriminate between coagulation dynamics and sedimentation dynamics.

14. The method according to claim 9, wherein the time variation in the optical transmission of said sample is determined from said time series of two-dimensional images.

15. The method according to claim 9, wherein said two-dimensional images are acquired at a rate greater than or equal to 0.5 Hz.

16. The method according to claim 9, wherein the fluid is whole blood, a blood fraction, or blood plasma.

* * * * *

UNITED STATES PATENT AND TRADEMARK OFFICE
CERTIFICATE OF CORRECTION

PATENT NO. : 9,442,125 B2  
APPLICATION NO. : 14/925495  
DATED : September 13, 2016  
INVENTOR(S) : Pouteau et al.

Page 1 of 1

It is certified that error appears in the above-identified patent and that said Letters Patent is hereby corrected as shown below:

On the Title Page

Insert the following:  
--(30)   Foreign Application Priority Data  
Mar. 26, 2009   (FR) .......................... 09 01435--.

Signed and Sealed this  
Twenty-third Day of May, 2017

Michelle K. Lee  
*Director of the United States Patent and Trademark Office*